(12) United States Patent
Aylor et al.

(10) Patent No.: US 9,814,911 B2
(45) Date of Patent: Nov. 14, 2017

(54) SKIN AND HAIR TREATMENTS

(76) Inventors: Robert Benson Aylor, Cincinnati, OH (US); Leigh Heather Makover, Ft. Myers, FL (US)

( * ) Notice: Subject to any disclaimer, the term of this patent is extended or adjusted under 35 U.S.C. 154(b) by 0 days.

(21) Appl. No.: 13/507,607

(22) Filed: Jul. 14, 2012

(65) Prior Publication Data
US 2013/0018109 A1    Jan. 17, 2013

Related U.S. Application Data

(60) Provisional application No. 61/572,443, filed on Jul. 15, 2011.

(51) Int. Cl.
| | |
|---|---|
| *A61K 31/045* | (2006.01) |
| *A61K 31/015* | (2006.01) |
| *A61K 8/34* | (2006.01) |
| *A61P 25/06* | (2006.01) |
| *A61P 25/00* | (2006.01) |
| *A61P 17/14* | (2006.01) |
| *A61Q 7/00* | (2006.01) |
| *A61Q 19/08* | (2006.01) |
| *A61Q 19/00* | (2006.01) |
| *A61Q 5/02* | (2006.01) |

(52) U.S. Cl.
CPC ............ *A61Q 19/08* (2013.01); *A61K 8/342* (2013.01); *A61K 31/015* (2013.01); *A61K 31/045* (2013.01); *A61Q 5/02* (2013.01); *A61Q 7/00* (2013.01); *A61K 2800/74* (2013.01)

(58) Field of Classification Search
CPC ............................ A61K 31/045; A61K 31/015
See application file for complete search history.

(56) References Cited

U.S. PATENT DOCUMENTS

| | | | |
|---|---|---|---|
| 4,371,461 A | 2/1983 | Jones et al. | |
| 4,933,371 A * | 6/1990 | Hink et al. | 514/739 |
| 4,982,874 A * | 1/1991 | Pringle | 222/78 |
| 6,203,796 B1 * | 3/2001 | Papaprodromou | 424/745 |
| 6,323,166 B1 * | 11/2001 | Kamiya | 510/119 |
| 2004/0126415 A1 * | 7/2004 | Lu | A61K 9/7053 424/449 |
| 2010/0209484 A1 * | 8/2010 | Choi | A61K 31/422 424/449 |
| 2011/0092493 A1 | 4/2011 | Levi et al. | |
| 2011/0144191 A1 | 6/2011 | Mclellan et al. | |

OTHER PUBLICATIONS

Velluti et al. in International Journal of Food Microbiology 89 (2003) 145-154.*
Tsai et al. in Contact Dermatitis, 1999, 41 311-314.*
Kunta et al. in Journal of Pharmaceutical Sciences, 86(12), 1369-1373 (1997).*
Villalon et al. in Current Vascular Pharmacology 2003, 1(1) 71-84 (Abstract).*

* cited by examiner

*Primary Examiner* — Dennis Heyer

(57) ABSTRACT

Linalool and other materials which are skin penetrating vasodilators or which can be made to have such properties are applied, either by themselves or in skin treatment compositions, to the skin of the head and especially the back of the neck to prevent or alleviate the effects of migraine headaches or applied to sore muscles or ligaments to aid in minimizing the soreness, or are applied to wrinkled and/or old looking skin on the face, neck, torso, or extremities, other than on the hands, to minimize wrinkles and/or improve the skin's appearance and/or are applied to the head to grow hair on the head or prevent hair loss.

11 Claims, No Drawings

SKIN AND HAIR TREATMENTS

RELATED APPLICATION

This application claims the benefit of the filing date of applicants' provisional U.S. Patent Application No. 61/572,443, filed Jul. 15, 2011, and entitled "PAIN TREATMENT", said application being incorporated herein by reference.

BACKGROUND OF THE INVENTION

Field of the Invention

The invention relates to the improvements in minimizing the occurrence and severity of pain, including muscle, tendon, ligament, etc. pains and especially migraine headaches; either alternately or additionally, providing appearance benefits such as wrinkle reduction and hair maintenance; and to methods, compositions, etc. for providing such improvements.

Description of Related Art

U.S. Pat. No. 4,371,461, Jones, et al., issued Feb. 1, 1983, claims: A liquid detergent composition containing by weight: (a) from about 10% to about 50% of a detergent surfactant; (b) from 0% to about 15% of a suds stabilizing nonionic surfactant selected from the group consisting of amine oxides, fatty acid amides, and the ethylene oxide condensates of alcohols and alkyl phenols; (c) from about 0.01% to about 0.6% of linalool; and (d) balance water and alcohol said composition being essentially free of aldehydes and primary alcohols with structures like linalool and having a pH in use of less than about 8.5.

The patent does not mention treating migraine headaches and teaches the composition primarily for cleaning dishes while providing a good feel for the hands.

US Pat. Appl. 20110092493, Levi, Clark et al., filed Apr. 21, 2011 teaches formulations for transdermal delivery of promethazine which can be used for pain, e.g., from migraine headaches. There is an incidental disclosure of linalool as an optional ingredient.

US Pat. Appl. 20110144191, McLellan, Alexander, et al., filed Jun. 16, 2011, teaches compositions comprising terpene compounds for the treatment of negative sensory phenomena. The compositions mention linalool as an optional ingredient and mention migraine headaches.

There are many Internet sites that document in great detail studies that concern linalool, its safety and uses, including:

--- http://www.anandaapothecary.com/aromatherapy-essential-oils-news/2009/05/linalool-common-essential-oil.html and
http://www.inchem.org/documents/sids/sids/78706.pdf

---

Linalool is a registered pesticide. See: http://www.epa.gov/oppsrrd1/registration_review/linalool/index.htm
and the toxicity is summarized at: http://www.pesticideinfo.org/Detail_Chemical.jsp?Rec_Id=PC35450

In addition to the above, the art contains large numbers of references to linalool, a common natural compound, since it is used in flavors and perfumes of many kinds.

There is no mention in literature relating to treatment of migraine headaches using linalool as an active ingredient and at present the literature suggests that there is no effective treatment for migraine headaches. A useful summary of migraine headaches can be found on the internet at:

--- http://www.bing.com/health/article/healthwise-1250004820/Migraine-Headaches-Topic-Overview?q=migraine+headaches

---

The contents of all of the above internet sites during June 2011 are incorporated herein by reference.

As can be seen from the above art, the present invention meets a long felt need, especially for migraine headaches where, previously, sufferers had to rely upon avoidance of things they wanted, and/or use expensive drugs that have undesirable side effects, while still not completely avoiding the problems caused by the headaches.

BRIEF SUMMARY OF THE INVENTION

The invention comprises a product for minimizing either: 1. a migraine headache or 2. muscle, ligament, or tendon pain, comprising an effective amount of a compound that is a mild vasodilator that can penetrate the skin in a container in association with instructions either to apply the product to the head and/or neck to treat a migraine headache or to apply the product to the skin above the site of the muscle, ligament or tendon pain and/or methods of treating such pain and/or migraine headaches by topical application of such compounds and/or products. The invention also uses these products and methods for minimizing wrinkles, improving the skin's condition, and increasing hair growth and/or minimizing hair loss where the compounds/products are applied.

Linalool and other compounds having similar properties including skin penetration and vasodilation can prevent, or alleviate pain, especially the pain associated with migraine headaches, especially when applied to the skin at appropriate locations, e.g., on the head and especially the back of the neck for migraine headaches and on the skin adjacent the individual muscle, tendon, ligament, etc. where the pain occurs for muscles, etc. The mode of action is not clear, but it is believed to be based at least in part upon the fact that linalool is known to be a mild vasodilator that can penetrate the skin to promote blood flow, especially in the absence of primary alcohols with structures similar to linalool which is a tertiary alcohol and the other ingredients are believed to have similar properties.

Since migraine headaches are accompanied by restricted flow of blood in the back of the neck, it is believed some dilation of the blood vessels in that area is at least partly responsible for providing relief. In general, other, preferably mild, vasodilators that can penetrate, or be made to penetrate the skin, can provide relief. Limonene, for example is also a skin penetrating vasodilator, although it is known to cause skin sensitivity, and has been shown to cause tumors in mice according to published information.

Thus the invention with respect to treatment of migraine headaches can be as broad as the use of vasodilators which can penetrate the skin being applied to the head and especially the back of the neck in effective amounts to prevent and/or alleviate the pain of migraine headaches.

In addition to dilation of the blood vessels, linalool is present in lavender oil that is known to provide a feeling of relaxation. Thus, a change to a more relaxed mood from the use of relatively large amounts of linalool can be part of the reason for its ability to prevent and alleviate the effects of migraine headaches. Linalool is the preferred compound since its safety profile is the best and has demonstrated effectiveness.

The improvement in blood flow improves skin condition and helps in the treatment of muscle, tendon, ligament, etc. aches and pains in the same way that heat helps by improving blood flow.

The increase in blood flow can improve the appearance and condition of skin. It has been shown that even the large wrinkles on the brow in older individuals can be minimized by constant treatment. As stated above, hair growth can be promoted on the head and hair loss minimized.

DETAILS OF THE INVENTION

The invention uses actives that are vasodilators, preferably mild vasodilators, especially linalool which also provides desirable mood adjustment, or functionally equivalent compounds having similar structures to linalool, especially at relatively high levels, due to the inherent safety of the compounds, which penetrate the skin, wherein the method of treatment comprises applying said compounds to the skin near the site of the pain being treated, and on the head, especially the back of the neck for migraine headaches.

The invention also relates to minimizing wrinkles and/or improving skin condition and appearance and/or to minimizing hair loss and/or promoting hair growth on the head.

Linalool

Linalool, the preferred active, is a natural ingredient used in many foods as a flavoring and in many perfumes as an odorant. The safety profile of linalool makes it a preferred option for treatments. There are no alternatives to the present invention for effective treatment of migraines and especially with a good safety profile. Hair growth can sometimes be achieved, e.g., with a product like minoxidil, but not with the same degree of safety.

Linalool is a tertiary alcohol. The linalool, or other tertiary alcohol is typically present at a level of from more than 0.01%, but for effectiveness, in levels of at least ½%, 1%, 2% etc. to about 5% by weight by weight for migraine treatment in a composition that is applied to the skin to provide sufficient active ingredients. For convenience, adding the active by volume can be useful when modifying existing compositions. Linalool's density of about 0.86 gram per cubic centimeter at normal room temperature provides a reasonable equivalence for volume and weight.

The minimum effective level for any composition can be determined for any particular use by creating a dose/response curve under actual conditions. However, it will normally be desirable to have a level of active set as high as safety/expense allow, especially when alleviation of pain is the goal. For rapid relief of pain and promoting skin appearance and hair maintenance/growth, higher levels of active (1, 2, 3, 4, 5, or more, %) and more frequent applications can be used.

Compositions to be used herein are desirably free of other actives previously used for treating migraine headaches, muscle pain, or hair loss to avoid possible side effects and ingredients that irritate the skin and the compositions can desirably contain emollients that provide improved skin feel. Linalool and similar tertiary alcohols are relatively difficult to solubilize in water but higher levels can be solubilized or can be formed into emulsions.

The compositions containing the preferred tertiary alcohols are preferably essentially free of aldehydes and the primary alcohols that are similar to the tertiary alcohols. The preferred tertiary alcohols are linalool, tetrahydrolinalool, 4-terpineol, Aprol-100 (3,6-dimethyl octane-3-ol), alpha-terpineol, ocimenol and nerolidol. Linalool, being safe and effective, is the most preferred.

Limonene can also be used as an active.

The linalool also provides skin appearance benefits, especially on the face and head areas, thus it is appropriate to recommend compositions such as shampoos for continual usage not only on the scalp, but also on the rest of the head to avoid migraine headaches and on other body parts as well for other benefits. The other vasodilators can also provide such benefits.

Linalool also aids in the treatment of other pains such as those in muscles, tendons, and ligaments which are typically helped by heat, since, like heat, linalool improves blood flow.

Thus, the methods of relieving pain involve the application of an effective amount of a skin penetrating vasodilator compound or composition to the area where the pain is present or where the pain can be treated. Linalool is the preferred compound.

For skin application, to improve skin appearance and/or condition and to improve hair retention and/or growth on the head, the compositions can contain other ingredients such as emollients, hydration ingredients, ingredients for defoliation of the skin, etc. as discussed hereinafter.

Application Means

There are many means by which the vasodilators can be applied to the skin. These include compositions for skin treatment such as shampoos, skin conditioners, etc., that can have other functions and mechanical dispensing means such as sprays, pads, etc.

Especially desirable options for treatment of pain include pads or patches for application to a specific area that provide an extended treatment. Such devices have been disclosed in, e.g.: U.S. Pat. No. 5,834,011 for treatment of tobacco smoking addiction, Rose, et al., issued Nov. 10, 1998; U.S. Pat. No. 5,891,101, Wilcox et al., issued Apr. 6, 1999; and U.S. Pat. No. 5,503,844, Kwiatek et al., issued Apr. 2, 1996. Other applicators are disclosed in U.S. Pat. No. 7,108,440, Gruenbacher et al. issued Sep. 19, 2006. All of said patents are incorporated herein by reference, especially for the specific disclosures of the applicators.

Spray containers of all types can be used including the normal pressurized containers, trigger sprayers, etc.

In general, the direct application of the pure material is less desirable than application in a composition that provides a diluted form, and especially in aqueous compositions, which provide safe, cheap dilution for application to a wider area. The dilute compositions will typically contain a solubilizer and/or emulsifier to help maintain the composition in stable form. If the composition is not stable the composition will need to be shaken before use and will require instructions to shake before use.

Compounds, like esters of linalool that will break down over time, such as photo labile esters, can provide extended treatment.

Compositions

The compositions of the invention can contain, in addition to the linalool or equivalent compounds, all active materials, additives and adjuvants known for use in skin and hair treatment compositions that do not interfere with the action of the active vasodilators. These are, for example, gelling agents and/or thickeners, anionic polymers, surfactants, hydrating agents, emollients, hydrophilic or lipophilic active compounds such as ceramides, agents against free radicals, sequestrants, antioxidants, skin defoliants, preservatives, alkalizers or acidifiers, perfumes, fillers, colorants, volatile or non-volatile, modified or non-modified silicones, and reducing agents, so long as they do not interfere with the action of the linalool or equivalent compounds.

The proportions of different additives that are used in such compositions are those that would be used by a person skilled in the art. Suitable types of compositions include shampoos and skin conditioners.

Shampoos

In many cases, the shampoo compositions will contain at least one surfactant, in which case anionic as well as zwitterionic, ampholytic, non-ionic and cationic surfactants are suitable. The minimum amount of surfactant in increasing order of preference is either 1%, 2%, and 5% by weight, and the maximum amount of surfactant in increasing order of preference is 35%, 25%, and 10% by weight. Where the main reason for using the shampoo is to prevent migraine headaches, the amount of surfactant and therefore cleaning is not the main consideration.

Anionic Surfactants

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853, Collins, Royal D., issued Aug. 24, 1984 said patent being incorporated herein by reference.

Other anionic materials include phosphates such as monoalkyl, dialkyl, and trialkylphosphate salts.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Non-Ionic Surfactants

Nonionic surfactants useful herein include those selected from the group consisting of alkyl glucosides, alkyl polyglucosides, polyhydroxy fatty acid amides, alkoxylated fatty alcohols and fatty acid esters, sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

Amphoteric Surfactants

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, $C_{12\text{-}14}$ glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Non-limiting examples of such anionic, nonionic, amphoteric, zwitterionic, etc. surfactants useful in the compositions of the present invention are disclosed in McCutcheon's, Detergents and Emulsifiers, North American edition (1986), published by allured Publishing Corporation; McCutcheon's, Functional Materials, North American Edition (1992); U.S. Pat. No. 3,664,961, Norris, issued May 23, 1972, U.S. Pat. No. 3,929,678, Laughlin et al., issued Dec. 30, 1975, U.S. Pat. No. 4,222,905, Cockrell, issued Sep. 16, 1980, and in U.S. Pat. No. 4,239,659, Murphy, issued Dec. 16, 1980, all of said references and disclosures being incorporated herein by reference.

Non-Lathering Surfactants

A wide variety of non-lathering surfactants are useful herein. The composition of the present invention can comprise a sufficient amount of one or more non-lathering surfactants to emulsify the dispersed phase to yield an appropriate particle size and good application properties on wet skin.

Non-limiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

Furthermore, the agents according to the invention can preferably contain a conditioning agent selected from the group consisting of cationic surfactants, cationic polymers, alkylamidoamine, paraffin oils, vegetable oils, and synthetic oils.

Preferred conditioning agents can be cationic polymers. These are usually polymers that contain a quaternary nitrogen atom, for example, in the form of an ammonium group.

Preferred Cationic Polymers are, for Example: quaternized cellulose derivates, such as are commercially available under the names Celquat® and Polymer JR®. The compounds Celqua® H 100, Celquat®L 200- and Polymer JR® 400 are preferred quaternized cellulose derivates; polymeric dimethyldiallylammonium salts and their copolymers with acrylic acid as well as esters and amides of acrylic acid and methacrylic acid. The products commercially available under the names Merquat.© 100 (poly(dimethyldiallylammonium chloride)), Merquat® 550 (dimethyldiallylammonium chloride-acrylamide copolymer), and Merquat® 280 (dimethyldiallylammonium chloride-acrylic acid copolymer) are examples of such cationic polymers; [0080] copolymers of vinylpyrrolidone with quaternary derivates of dialkylaminoacrylate and methacrylate, for example, with diethylsulfate-quaternised vinylpyrrolidone-dimethylaminomethacrylate copolymers. Such compounds are available commercially under the names Gafquat®734 and Gafquat® 755. [0081] vinylpyrrolidone-methoimidazolinium chloride copolymers that are marketed under the name Luviquat®; [0082] quaternized polyvinyl alcohol as well as polymers with quaternary nitrogen atoms in the main polymer chain that are known as Polyquaternium 2, Polyquaternium 17, Polyquaternium 18, and Polyquaternium 27.

Particularly preferred are cationic polymers of the four first named groups, quite especially preferred are Polyquaternium-2, Polyquaternium-10, and Polyquaternium-22.

Also suitable as conditioning agents are silicone oils, especially dialkyl- and alkylarylsiloxanes, for example, dimethylpolysiloxane and methylphenylpolysiloxanes, as well as their alkoxylate and quaternized analogues. Examples of such silicones are the products marketed by Dow Corning under the names DC 190, DC 200, DC 344, DC 345, and DC 1401 as well as the trade products Q2-7224 (manufacturer: Dow Corning; a stabilized trimethylsilylamodimethicone), Dow Corning 929 Emulsion (containing a hydroxyamino-modified silicone, that is also called Amodimethicone), SM-2059 (manufacturer: General Electric), SLM-55067 (manufacturer: Wacker), and Abil®Quat 3270 and 3272 (manufacturer: Th. Goldschmidt; diquaternary polydimethylsiloxane, Quaternium-80).

Equally usable as conditioning agents are paraffin oils, synthetic oligomeric alkenes as well as vegetable oils such as jojoba oil, sunflower oil, orange oil, almond oil, wheat germ oil, and peach stone oil.

Likewise suitable hair conditioning compounds are phospholipids, for example, soy lecithin, egg lecithin, and cephalines.

Further active compounds, adjuvants and additives are, for example: nonionic polymers such as vinylpyrrolidone/vinylacrylate copolymers, polyvinylpyrrolidone and vinylpyrrolidone/vinyl acetate copolymers, and polysiloxanes; zwitterionic and amphoteric polymers such as acrylamidopropyltrimethylammonium chloride/acrylate copolymers and octylacrylamide/methylmethacrylate/tert-butylaminoethylmethacrylate/2-hydroxypropylmethacrylate copolymers; anionic polymers, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methylvinyl ether/maleic acid anhydride copolymers, and acryl acid/ethyl acrylate/N-tert.butylacrylamide terpolymers; thickening agents such as agar, guar gum, alginate, xanthan gum, gum arabic, karaya gum, carob bean flour, linseed gum, dextrans, cellulose derivatives, e.g., methylcellulose, hydroxyalkylcellulose and carboxymethylcellulose, starch fractions and derivatives such as amylose, amylopectin and dextrins, clays such as bentonite or fully synthetic hydrocolloids such as polyvinyl alcohol; structuring agents such as maleic acid and lactic acid; hair conditioning compounds such as phospholipids, for example, soy lecithin; egg lecitin and cephalines, protein hydrolysates, especially elastin, collagen, keratin, milk protein, soy protein and wheat protein hydrolysates, their condensation products with fatty acids as well as quaternized protein hydrolysates; perfume oils, dimethylisosorbide, and cyclodextrins; solvents and solubilizers such as ethanol, isopropanol, ethylene glycol, propylene glycol, glycerol, and diethylene glycol; fiber structure improvement agents, especially mono-, di- and oligosaccharides such as glucose, galactose, fructose, D-fructose, and lactose; quaternary amines such as methyl-1-alkylamidoethyl-2-alkylimidazolinium methosulfate; foam inhibitors such as silicones, dyes for coloring the agent; active antidandruff agents such as piroctone olamine, zinc pyrithione, and climbazole; photoprotective agents, especially derivatized benzophenones, cinnamic acid derivatives, and triazines; buffers, for example normal acids, especially benefit acids and bases; plant extracts such as the extracts from green tea, oak bark, stinging nettles, witch hazel, hops, chamomile, burdock root, horsetail, hawthorn, lime blossom, almonds, aloe vera, pine needles, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, marshmallow, meristem, ginseng, and ginger root; cholesterol; consistency regulators such as sugar esters, polyol esters or polyol alkyl ethers, fats and waxes such as spermaceti, beeswax, montanin wax and paraffins, fatty acid alkanolamides; chelating agents such as EDTA, NTA, .beta.-alanine diacetic acid and phosphoric acids; swelling and penetration agents such as glycerol, propylene glycol monoethyl ether, carbonates, hydrogen carbonates, guanidines, ureas as well as primary, secondary, and tertiary phosphates; opacifiers such as latex, styrene/PVP, and styrene/acrylamide copolymers; pearlescents such as ethyleneglycol mono- and distearate as well as PEG-3 distearate, pigments; stabilizers for hydrogen peroxide and other oxidizing agents; aerosol propellants such as propane-butane mixtures, N20, dimethyl ether, $CO_2$, and air; antioxidants.

Other components as well as the amounts of compounds can be found in the comprehensive reference books such as "Kh. Schrader, Grundlagen and Rezepturen der Kosmetika, 2. edition, Huthig Buch Verlag, Heidelberg, 1989.", said reference being incorporated herein by reference.

Skin Conditioner Products

Skin conditioner products typically contain less water and can be formulated to contain more of the active. The higher active levels are desirable for greater efficacy, especially for treating migraine headaches once they are identified. Some individuals can tell when a migraine headache is going to occur when they experience a migraine aura.

Compositions for use in direct application to skin can contain a wide range of levels of actives. However, desirably, the level of active of this invention is either about 5%, about 4%, 3%, 2%, or about 1% by volume when the active is added to existing products, to minimize the problems associated with making stable compositions, especially aqueous compositions. Volume is used for convenience in adding actives since compositions can have different specific gravities and the use of a volume measurement avoids having to determine the specific gravity. The surfactants and emulsifiers described hereinbefore are suitable for keeping the compositions stable. Instructions for "shaking before use" are desirable when the compositions are unstable or borderline unstable.

Compositions that contain disclosures of materials that can be used include those described in published United States Patent Applications 2005/0214332 by Osborne, Rosemarie; et al., Sep. 29, 2005, and United States Patent Application 20050019356 by Bissett, Donald Lynn; et al., Jan. 27, 2005, said patent applications being incorporated herein by reference.

Other compositions that contain disclosures of materials that can be used include those described in U.S. Pat. Nos. 5,939,082, 5,939,082, Aug. 17, 1999, said patent being incorporated by reference.

Some substituted acids, e.g., alpha hydroxyl acids are known to have the property of facilitating the removal of dead skin. Since improved blood flow primarily benefits live skin cells, the removal of dead skin is a desirable additive effect.

It is also possible to arrange for more continuous exposure to linalool by making and including in the formula an extended exposure version of the active, e.g., time release capsules or labile compounds that break down over time to release the active, e.g., labile esters such as a photo labile ester of the type described in United States Patent Application 20020094938, Dykstra, Robert Richard; et al., Jul. 18, 2002, said patent application being incorporated herein by reference.

Examples of skin conditioner products and suitable ingredients that can be used in formulating such products can be found in U.S. Pat. No. 6,551,604, Beck et al., issued Apr. 22, 2003 and incorporated herein by reference. The patent includes specific disclosures of compounds for: "chronically regulating skin condition (col. 5, line 19 et seq.); optional components (col. 8, line 57 et seq,); emollients (col. 9, line 19 et seq.); humectants (col. 10, line 36 et seq.); emulsifiers/surfactants (col. 10, line 63 et seq.); thickening agents (col. 13, line 24 et seq.); anti-inflammatory agents (col. 14, line 17 et seq.); sunscreens and sunblocks (col. 14, line 43 et seq.); antioxidants/free radical scavengers (col. 14, line 63 et seq.); chelators (col. 15, line 19 et seq.); desquamation agents/exfoliants (col. 15, line 31 et seq.); skin lightening agents (col. 15, line 50 et seq.); and Examples of compositions (col. 16. Line 59, et seq.), all of said patent and specifically the ingredients and examples being incorporated herein by reference.

Other compounds that can be useful include farnesol, phytantriol, and mixtures thereof.

As indicated in the said patent, a wide variety of surfactants can be useful in skin conditioning products such as massage compositions and other skin softening and conditioning compositions useful herein. The surfactants provide for, e.g., emulsification of a dispersed phase, acceptable spreading, and in use properties for non-lathering systems. For cleansing applications, the surfactant phase also serves to clean the skin and provide an acceptable amount of lather for the user. The composition preferably contains, in descending order, no more than about 50, about 30 weight percent, about 15 weight percent, and about 5 weight percent of surfactant depending on the end use, concentration, etc.

The composition preferably contains, in descending order, at least about 5, about 3 weight percent, about 1 weight percent, and about 0.1 weight percent of surfactant, again depending on the concentration, etc. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test. The personal care compositions preferably produces a Flash Lather Volume of at least 100 ml, preferably greater than 200 ml, more preferably greater than 300 ml as described in the Lathering Volume Test.

Preferable surfactants for use in skin conditioning compositions include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757, to McAtee et al., issued Aug. 28, 2001 and incorporated herein by reference.

Other examples of suitable surfactants and conditioning agents include those disclosed above for shampoos.

There are several commercial emulsifier mixtures that are useful in some embodiments. Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl-)-N—N-Dimethyl,N—C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, peg-75 stearate, ceteth-20 and steareth-20) from Gattefosse.

The compositions of the present invention, in some embodiments, can further include one or more thickening/aqueous phase stability agents. Because different stability agents thicken with different efficiencies, it is difficult to provide an accurate compositional range, however, when present, the composition preferably comprises no more than about 10 weight percent, more preferably no more than about 8 weight percent, and still more preferably no more than about 7 weight percent of the personal care composition. When present, the thickening/aqueous phase stability agent preferably comprises at least about 0.01 weight percent, more preferably at least about 0.05 weight percent, and still more preferably at least about 0.1 weight percent of the personal care composition. A better method of describing the Stability Agent is to say that it must build viscosity in the product. This can be measured using the Stability Agent Viscosity Test. Preferably, the stability agent produces a viscosity in this test of at least about 1000 cps, more preferably at least about 1500 cps, and still more preferably at least about 2000 cps.

Non-limiting examples of thickening agents useful herein include carboxylic acid polymers such as the carbomers (such as those commercially available under the tradename CARBOPOL®900 series from B.F. Goodrich; e.g., CARBOPOL®954). Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as CARBOPOL®1342, CARBOPOL®1382, PEMULEN TR-1, and PEMULEN TR-2, from B.F. Goodrich.

Other non-limiting examples of thickening agents include crosslinked polyacrylate polymers including both cationic and nonionic polymers; polyacrylamide polymers; polysaccharides; gums; and modified starches.

Especially desirable are: nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multiblock copolymers include HYPAN SR150H, SS500V, SS500W, SSSA100H, from Lipo Chemicals, Inc., (Patterson, N.J.).

Non-limiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the tradename NATROSEL®CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS11 from Michel Mercier Products Inc. (Mountainside, N.J.).

Non-limiting examples of gums useful herein include hectorite, hydrated silica, xantham gum, and mixtures thereof.

Acrylate modified starches such as WATERLOCK® from Grain Processing Corporation can be used. Hydroxypropyl starch phosphate, tradename STRUCTURE XL from National Starch is another example of a useful modified starch, and other useful examples include ARISTOFLEX HMB (Ammonium Acrylodimethyltaruate/Beheneth—25 Methacrylate Crosspolymer) from Clariant.

The compositions can also contain organic cationic deposition polymer Concentrations of the cationic deposition polymer preferably range from about 0.025% to about 3%, more preferably from about 0.05% to about 2%, even more preferably from about 0.1% to about 1%, by weight of the personal care composition.

Suitable cationic deposition polymers for use in the compositions contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal cleansing composition, which pH will generally range from about pH 4 to about pH 9, preferably between about pH 5 and about pH 8.

Non-limiting examples of cationic deposition polymers for use in the personal care composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non-crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymers in the personal care composition ranges from about 0.025% to about 5%, preferably from about 0.1% to about 3%, more preferably from about 0.2% to about 1%, by weight of the composition.

A non-limiting example of a commercially available synthetic cationic polymer for use in the cleansing compositions is polymethyacrylamidopropyl trimonium chloride, available under the trade name POLYCARE 133, from Rhodia, Cranberry, N.J., U.S.A.

Shiny Particles

Non-limiting examples of the optional interference pigments useful herein include those supplied by Persperse, Inc. under the trade name PRESTIGE®, FLONAC® supplied by EMD Chemicals, Inc. under the trade names TIMIRON®, COLORONA®, DICHRONA® and XIRONA® and supplied by Engelhard Co. under the trade names FLAMENCO®, TIMICA®, and DUOCHROME®.

A second class of interference pigment is based on cholesteric liquid crystal, e.g. HELICONE® HC supplied by KOBO products. HELICONE® HC is composed of transparent platelets of polyacrylates with a helical superstructure. As part of this structure, cigar-shaped liquid crystal molecules are fixed into layers of parallel rows. Each layer has a slightly different molecular orientation and the distance between two layers with the same molecular orientation defines as the "pitch", which determines the color. This type pigment is hydrophobic. Therefore, they can be used without surface treatment.

Other Optional Ingredients

Additional non-limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol) and antibacterial agents and mixtures thereof. These materials can be used at ranges sufficient to provide the required benefit.

Adhesive materials, such as cross-linked silicone resin-dimethicone blends, as well as acrylate based adhesives and other commonly used film-forming materials such as the modified PVP polymers sold under the tradename GANEX from ISP can also be used in the present invention.

Skin and Hair Care Benefits

The compounds and compositions of the invention can provide skin appearance and hair appearance benefits. The preferred linalool products provide improved blood flow to the skin and hair. The skin looks healthier and has better elasticity, thus the skin has less wrinkles, especially for the time immediately after the product is used. Continuous use provides a desirable, healthy skin appearance and helps to remove wrinkles. The products herein when they contain larger amounts of the linalool or other similar active, and when they are used regularly over a period of time can minimize or remove most wrinkles, including even the large wrinkles commonly found on the foreheads of older people. The benefits can improve the performance of other skin enhancing ingredients in skin conditioning and cleaning products, especially those used on the head and especially on the face, but also on the torso, limbs and neck where the skin can appear aged, including rough and wrinkled.

These skin treatment compositions which contain more linalool can be used to treat muscle and ligament pains by improving blood flow to the muscles and ligaments as discussed hereinbefore. The benefit is similar to the benefit provided by heat treatments. For such products, the level of the linalool can be higher with emulsifiers being used to increase the amount of linalool that can be incorporated while maintaining homogeneity. Typically, such products preferably have more than about a half percent of linalool and more preferably at least approximately one percent linalool by weight.

As discussed before, an especially valuable benefit can be obtained by the use of compositions containing more linalool and/or more frequent applications of the compositions to the heads of people who are losing, or who have lost hair. The compositions, which are quite safe, when used more frequently and/or for longer periods of time, have been shown to promote hair growth even on people who have had hair loss, e.g., male pattern baldness for some period of time. The level of active and frequency of treatment can be gradually increased until the desired result is obtained.

The linalool products that are preferred herein provide especially desirable perfume effects and mood enhancing effects.

The invention also comprises the method of finding the most effective compounds and/or levels of said compounds for helping individuals suffering from migraine headaches or muscle, ligament, or tendon pain to provide a benefit selected from treating migraine headaches, preventing migraine headaches, helping to relieve muscle pain, helping to relieve tendon pain, helping to relieve ligament pain, in which compounds including limonene, linalool, tetrahydro-linalool, 4-terpineol, Aprol-100 (3,6-dimethyl octane-3-ol), alpha-terpineol, ocimenol and nerolidol are incorporated at levels of about 0.5%; about 1%; and about 1.5%, by weight, in a standard unscented shampoo or unscented standard skin conditioner composition and tested for at least one benefit with a representative group of said individuals.

The invention also comprises compositions comprising the effective compounds and levels of said compounds identified by the above method used to find the most effective compounds and the levels of said compounds.

EXAMPLES

Example 1

One individual who had suffered from migraines for several years and who had taken the prescription drug Prozac® with only limited benefits, started using a commercial product, Ivory Shampoo®, with approximately 1% by volume of linalool added. The prescription drug had not prevented migraine headaches, but after the shampoo was used on a regular basis, the migraine headaches no longer occurred. The individual stopped using Prozac due to problems associated with it and the migraine headaches did not return. Other commercially available shampoos containing little perfume with approximately 1% by volume of linalool added were substituted for the Ivory Shampoo with linalool and the benefit persisted. Another commercially available shampoo that has been used with about 1% by volume of linalool added is Botanical Nutrients® soyflower shampoo containing: water; extracts of geranium maculatum (geranium), Echinacea angustifolia (coneflower), and lavendula angustifolia (lavender); ammonium lauryl sulfate; decyl glucoside; cocoamide MEA; PPG-5-ceteth-10-phosphatel cocoamidopropyl betaine; fragrance; polyquatemium-7; glycerin; panthenol; hydrolyzed soy protein; isostearamidopropyl morpholine lactate; vitamin E; disodium wheat germamido PEG-2 sulfosuccinate; guar hydroxypropyl ammonium chloride; PEG-150 distearate; PEG-30 castor oil; PEG-12 dimethicone; benzophenone-4; disodium EDTA; diazolidinyl urea; methylparaben; and citric acid. Another shampoo that has been used is Bath & Body Works® Bio balancing shampoo.

Example 2

A second individual subject to migraine headaches with an aura also used the commercially available shampoos containing about 1% linalool without taking a prescription drug and found that the subject no longer experienced migraine headaches. When this individual stopped using the commercial shampoos containing about 1% linalool, a migraine headache was experienced. Since the commercial shampoo with about 1% linalool has been used again on a regular basis, there has been no migraine headache so far.

Example 3

A commercial skin conditioning product with low perfume level was modified by adding about 1% linalool for use in treating the back of the neck and/or the head to prevent and/or alleviate the effects of migraine headaches. The product is Bath & Body Works body lotion sold under the name "Dancing Waters" containing: water, glycerin; petrolatum; cetyl alcohol; cetearyl alcohol; dimethicone; perfume; ceteareth-20; shea butter; jojoba seed oil; tocopheryl acetate; isododecane; neopentyl glycol diheptonate; carbomer; tetrasodium EDTA; sodium hydroxide; disodium EDTA; BHT; benzyl alcohol; diazoldryl urea; methylparaben; propylparaben; benzyl benzoate; benzyl salicylate; cinnamyl alcohol; citral; citronelol; geranol; hexyl cinnamal; hydroxyphenyl 3-cyclohexene carboxaldehyde; limonene; linalool; butylphenyl methylpropanal; and alpha-isomethyl ionone. The limonene and linalool are present in the commercial product in only very limited amounts since they are among the last ingredients listed.

Example 4

The product of Example 3 is used to treat muscle and ligament pain with positive desirable effects.

Example 5

A product for direct application is prepared containing about 2% linalool emulsified with about 5% PROLIPID 141.

Example 6

The products of Examples 1-5 are prepared with limonene, tetrahydrolinalool, 4-terpineol, Aprol-100 (3,6-dimethyl octane-3-ol), alpha-terpineol, ocimenol and nerolidol replacing the linalool.

Example 7

The products of Examples 1-6 are used in a trigger spray bottle to spread the products.

Example 8

The products of Examples 1-6 are used in a pressurized spray bottle to spread the products.

Example 9

The products of Examples 1-6 are used in a product for attachment to the body using tape, said product containing a foam structure with the product inside, said product being open to the skin only to allow the products to be slowly applied to the skin to spread the products.

Example 10

Each of the products of Examples 1-6 are placed in containers containing the designation as a shampoo or skin treatment product and the information that the product can be used to either mitigate the effects of a migraine headache or to aid in the relief of muscle, tendon, or ligament pain.

Example 11

The product "oil-free moisture" sensitive skin sold by Neutrogena™ was modified by adding alternatively, 1%, 2%, and 3% linalool by volume. The product contains: water; glycerin; ethylhexyl palmitate; dimethicone; petrolatum; cyclomethicone; soybean glycine; soya stearols; isopropyl isostearate; cetyl alcohol; PEG-10 soy sterol; glyceryl stearate; PEG-100 stearate; C12-15 alkyl benzoate; carbomer; terasodium EDTA; sodium hydroxide; diazolidimyl urea; ethylparaben; methylparaben; and propylparaben.

These compositions, with gradual increase in the amount of linalool from 1% to 2% to 3% were applied to an individual's skin on the head, especially the forehead, body parts where wrinkles were present, and to the head, especially most of it to where there was male pattern baldness. The amount needed was typically from about 4 to about 6 squeezes on the push squeeze pump of the Neutrogena product.

After several months, and especially after gradual increase in the level of linalool in the product and increase in the frequency of the application to more than once a day, the forehead wrinkles became markedly less visible, the other smaller wrinkles essentially disappeared, and hair began showing visible growth in the area of male pattern baldness. The treatment is continuing with greater frequency of applications to determine how much can be applied without adverse effects. The treatment does not appear to have long lasting effects, since even a few days without treatment appear to have some negative consequences, especially for some wrinkled parts.

Example 12

The product of Example 3. was used as in the method of Example 11. and the benefits were observed, but the oils in the product became objectionable when, e.g., pillow slips absorbed the oils. The product was acceptable for use on the face and body, especially when used less frequently.

What is claimed is:

1. A method of treating or preventing a migraine headache, said method comprising administering to the skin of a subject in need thereof a composition comprising an effective amount of linalool, or a labile ester of linalool, wherein said composition is in the form of either a shampoo or a skin conditioning composition that is free of an effective amount of any other ingredient for treating a migraine headache, and wherein said composition is applied, to either the head, neck, or both head and neck to treat or prevent said migraine headache.

2. The method of claim 1 wherein said compound is linalool.

3. The method of claim 1 in association with the instructions for practicing the method.

4. The method of claim 3 where said instructions are found on a container for said composition.

5. The method of claim 1 wherein the treatment is with a skin treatment conditioning composition, wherein said effective amount is from about 1% to about 5% and the composition is applied after the onset of a migraine headache.

6. The method of claim 5 wherein said compound is linalool.

7. The method of claim 5 in association with instructions either to apply the product to the head, neck, or head and neck to alleviate the effects of said migraine headache.

8. The method of claim 7 where said instructions are found on a container for said composition.

9. The method of claim 1 wherein the composition is applied as a shampoo containing at least about 1% linalool to prevent the onset of a migraine headache.

10. The method of claim 9 in association with instructions either to apply the product to the head, neck, or head and neck to alleviate the effects of said migraine headache.

11. The method of claim 10 where said instructions are found on a container for said composition.

* * * * *